United States Patent
Belson

(10) Patent No.: US 10,426,930 B2
(45) Date of Patent: Oct. 1, 2019

(54) SYSTEMS AND METHODS FOR NEEDLE AND CATHETER ADVANCEMENT

(71) Applicant: Vascular Pathways, Inc., Naples, FL (US)

(72) Inventor: Amir Belson, Los Altos, CA (US)

(73) Assignee: Vascular Pathways, Inc., Salt Lake City, UT (US)

( * ) Notice: Subject to any disclaimer, the term of this patent is extended or adjusted under 35 U.S.C. 154(b) by 0 days.

(21) Appl. No.: 15/727,304

(22) Filed: Oct. 6, 2017

(65) Prior Publication Data

US 2018/0028788 A1    Feb. 1, 2018

Related U.S. Application Data

(63) Continuation of application No. 14/167,602, filed on Jan. 29, 2014, now Pat. No. 9,782,568.

(60) Provisional application No. 61/760,841, filed on Feb. 5, 2013.

(51) Int. Cl.
    *A61M 25/06* (2006.01)
    *A61M 29/00* (2006.01)

(52) U.S. Cl.
    CPC .... *A61M 25/0606* (2013.01); *A61M 25/0693* (2013.01); *A61M 29/00* (2013.01); *A61M 2025/0687* (2013.01)

(58) Field of Classification Search
    CPC .............. A61M 25/0606; A61M 25/0693
    See application file for complete search history.

(56) References Cited

U.S. PATENT DOCUMENTS

| | | | |
|---|---|---|---|
| 3,469,579 A | 9/1969 | Hubert | |
| 4,368,730 A | 1/1983 | Sharrock | |
| 4,767,407 A | 8/1988 | Foran | |
| 4,961,729 A | 10/1990 | Vaillancourt | |
| 5,242,410 A * | 9/1993 | Melker | A61M 25/06 604/164.1 |
| 6,273,871 B1 | 8/2001 | Davis et al. | |
| 6,726,659 B1 * | 4/2004 | Stocking | A61M 25/0606 604/164.01 |
| 2003/0153874 A1 | 8/2003 | Tal | |
| 2010/0094310 A1 | 4/2010 | Warring et al. | |
| 2010/0210934 A1 | 8/2010 | Belson | |
| 2011/0207157 A1 | 8/2011 | Gautier et al. | |
| 2011/0282285 A1 | 11/2011 | Blanchard et al. | |
| 2012/0157854 A1 | 6/2012 | Kurrus et al. | |

(Continued)

FOREIGN PATENT DOCUMENTS

WO    2014/123848 A1    8/2014

OTHER PUBLICATIONS

PCT/US2014/014577 filed Feb. 4, 2014 International search report and written opinion dated Apr. 16, 2014.

(Continued)

*Primary Examiner* — Edelmira Bosques
(74) *Attorney, Agent, or Firm* — Rutan & Tucker, LLP

(57) ABSTRACT

Intravenous access is achieved by introducing a catheter over an access needle which is initially present in the catheter. A tapered dilating element is positioned over the needle and provides a transition between the needle and a larger catheter lumen. The access needle is hollow and has a port which allows blood to flash back through a lumen of the catheter so that flashback can be observed on a catheter hub or the catheter itself.

4 Claims, 4 Drawing Sheets

(56) References Cited

U.S. PATENT DOCUMENTS

2012/0197200 A1    8/2012  Belson
2012/0316500 A1   12/2012  Bierman et al.

OTHER PUBLICATIONS

U.S. Appl. No. 14/167,602, filed Jan. 29, 2014 Advisory Action dated Dec. 15, 2016.
U.S. Appl. No. 14/167,602, filed Jan. 29, 2014 Final Office Action dated Nov. 16, 2015.
U.S. Appl. No. 14/167,602, filed Jan. 29, 2014 Final Office Action dated Sep. 27, 2016.
U.S. Appl. No. 14/167,602, filed Jan. 29, 2014 Non-Final Office Action dated Apr. 28, 2016.
U.S. Appl. No. 14/167,602, filed Jan. 29, 2014 Non-Final Office Action dated Jun. 5, 2015.
U.S. Appl. No. 14/167,602, filed Jan. 29, 2014 Notice of Allowance dated Jun. 8, 2017.

* cited by examiner

SYSTEMS AND METHODS FOR NEEDLE AND CATHETER ADVANCEMENT

CROSS-REFERENCE TO RELATED APPLICATIONS

This application is a continuation of U.S. patent application Ser. No. 14/167,602, filed Jan. 29, 2014, now U.S. Pat. No. 9,782,568, which claims the benefit of U.S. Provisional Patent Application No. 61/760,841, filed Feb. 5, 2013, each of which is incorporated herein by reference in its entirety.

BACKGROUND OF THE INVENTION

1. Field of the Invention

The present invention relates generally to methods and systems for performing venipuncture. More particularly, the present invention relates to a catheter and needle assembly which provides transcutaneous insertion of a large diameter catheter with a smaller diameter needle into a patient's vein with optional blood flashback.

The term "venipuncture" refers generally to the process of obtaining intravenous access for any one of a variety of purposes, including intravenous infusion, therapy, blood sampling, and the like. In the hospital, for example, venipuncture is commonly used to place a small intravenous catheter for delivering intravenous fluids, drug delivery, blood sampling and the like.

Venipuncture for catheter placement comprises placing a catheter over an access needle and inserting the access needle and catheter into a peripheral vein by penetrating the needle through the skin surface. One challenge to venipuncture is the introduction of large diameter catheter. Such introduction frequently requires use of a large diameter needle which can be painful for the patient. While it has been propose to grind down the needle tip to reduce discomfort (see, e.g. U.S. Pat. No. 4,767,407), such grinding significantly increases the cost of the needle. Alternatively, it has been proposed to taper the catheter tip down to the smaller needle diameter (see, e.g. U.S. Pat. No. 6,273,871), but such tapering reduces the catheter tip diameter which can be disadvantageous.

Another challenge to venipuncture is the delay in observing "flashback." In order to assure that the needle has reached the vein, the person inserting the needle will look for "flashback," i.e. a flow of blood through a lumen of the needle to a proximal end of the needle where the appearance of blood can be observed. As venous access needles can be long, there can be a perceptible delay between the actual entrance of the needle tip into the vein and the appearance of blood at the proximal end of the needle. While such delays will typically be relatively short, even very small delays between vein entry and the appearance of flashback can result in misplacement of the needle. For example, the needle may continue to be advanced and pierce the opposite wall of the vein. Such "overshoot" is obviously undesirable and should be avoided.

For these reasons, it would be desirable to provide improved apparatus and methods for performing venipuncture. In particular, it would be desirable to provide apparatus and methods which allow the use of reduced size needles for advancing relatively large diameter catheters. It would be further desirable to provide methods and apparatus for detecting blood which minimize the delay between actually entry of a needle tip into a vein and the appearance of blood flashback to the user introducing the needle and catheter. It would be further desirable if such improved methods and apparatus could be provided without the need to significantly modify the design or increase the cost of the catheter and/or access needle and with minimum change in the protocol used by those introducing the needles and catheters. At least some of these objectives will be met by the inventions described below.

2. Description of the Background Art

Needle and catheter assemblies are described in U.S. Pat. Nos. 3,469,579; 4,368,730; 4,767,407; 6,273,871; and U.S. Patent Publ. No. 2011/0208157. The following commonly owned applications, the full disclosures of which are incorporated herein by reference, also describe needle and catheter assemblies: U.S. Pat. Nos. 8,728,035; 8,721,546; and 8,690,833.

SUMMARY OF THE INVENTION

The present invention provides needle and catheter assemblies and methods for their use. In a first aspect of the invention, a needle and catheter assembly comprises a catheter body having a proximal end, a distal end, and a lumen therethrough. A needle is removably received in the catheter lumen, and the needle has a tissue-penetrating distal end and a lumen therethrough. A tapered dilator element is mounted coaxially over the exterior of the needle proximal of the distal tip. The needle has a cross-sectional area which is less than the cross-sectional area of the catheter lumen so that the tapered dilating element occupies an annular gap which would exist between the needle and the interior of the distal end of the catheter in the absence of the tapered dilating element.

In specific embodiments, the catheter body may consist of a tube having a single lumen configured to be positioned in a peripheral vein, and a proximal hub may be attached to the proximal end of the catheter body. The needle usually comprises a metal tube, and the tapered dilating element usually comprises a polymer collar. An exemplary access needle has a circular cross-section, and an exemplary catheter body lumen also has a circular cross-section, wherein the needle has an outer diameter in the range from 0.3 mm to 1.7 mm and the catheter body lumen has a diameter in the range from 0.4 mm to 2.8 mm. Usually, the inner diameter of the catheter body lumen is at least 20% larger than the outer diameter of the needle.

In a second aspect of the present invention, a method for introducing a catheter into a vein comprises providing a catheter as described above. A distal end of the access needle carries a distal tip of the catheter into the vein in a distal direction. The tapered dilator element provides a transition from the small needle diameter to the larger catheter diameter to reduce patient discomfort. After the catheter has entered the vein, the catheter is advanced over the needle (and optionally a guidewire) to a target location in the vein.

In a third aspect of the present invention, a needle and catheter assembly comprises a catheter body having a proximal end, a distal end, and a lumen therethrough. A needle is removably received in the catheter lumen, and the needle has a tissue-penetrating distal end, a lumen therethrough, and a flashback port proximal of the dilating element. The needle has a cross-sectional area which is less than the cross-sectional area of the catheter lumen so that blood which enters the needle can flow through the flashback port and into the catheter lumen where it will be visible through a transparent or translucent region in the catheter located near the distal end of the catheter.

In specific embodiments, the catheter body may consists of a tube having a single lumen configured to be positioned in a peripheral vein. A proximal hub may be attached to the proximal end of the catheter body, and the needle may have a circular cross-section and the catheter body lumen may have a circular cross-section, where the needle may have an outer diameter in the range from 0.3 mm to 1.7 mm and the catheter body lumen may have a diameter in the range from 0.4 mm to 2.8 mm. The inner diameter of the catheter body lumen is typically at least 20% larger than the outer diameter of the needle.

In a fourth aspect of the present invention, a method for introducing a catheter into a vein, comprises penetrating a distal end of a needle carrying a catheter into the vein in a distal direction. Blood enters a distal tip of the needle, flows proximally through a needle lumen to a flashback port on the needle, and then flows radially outwardly through the flashback port into an annular lumen in the catheter surrounding the needle. When the blood appears in a transparent or translucent region near the distal end of the catheter, the user may advance the catheter over the needle (and optionally a guidewire) until the catheter reaches a target location in the vein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
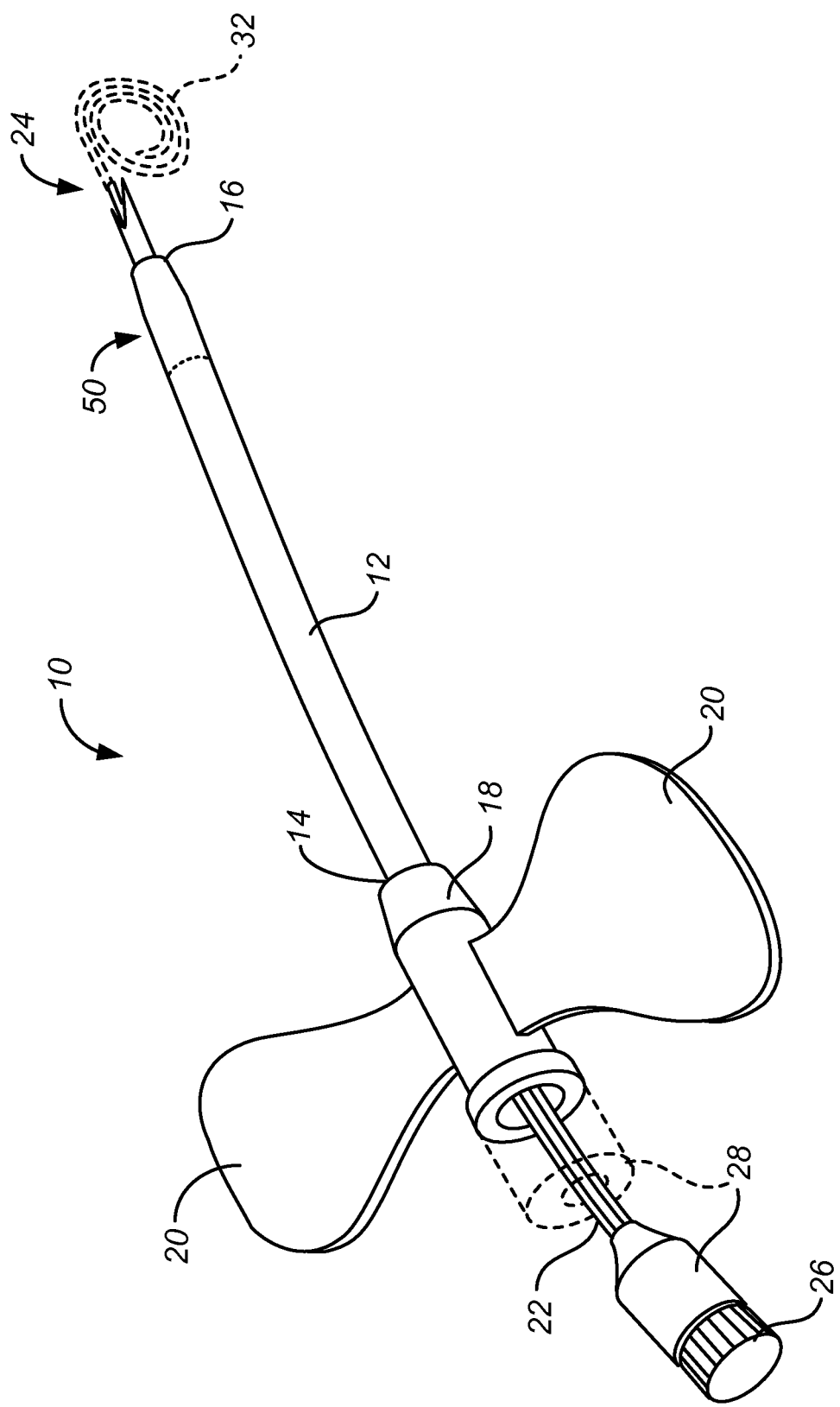
FIG. 1 is a perspective view of an intravenous catheter and a needle assembly constructed in accordance with the principles of the present invention.
Figure 2:
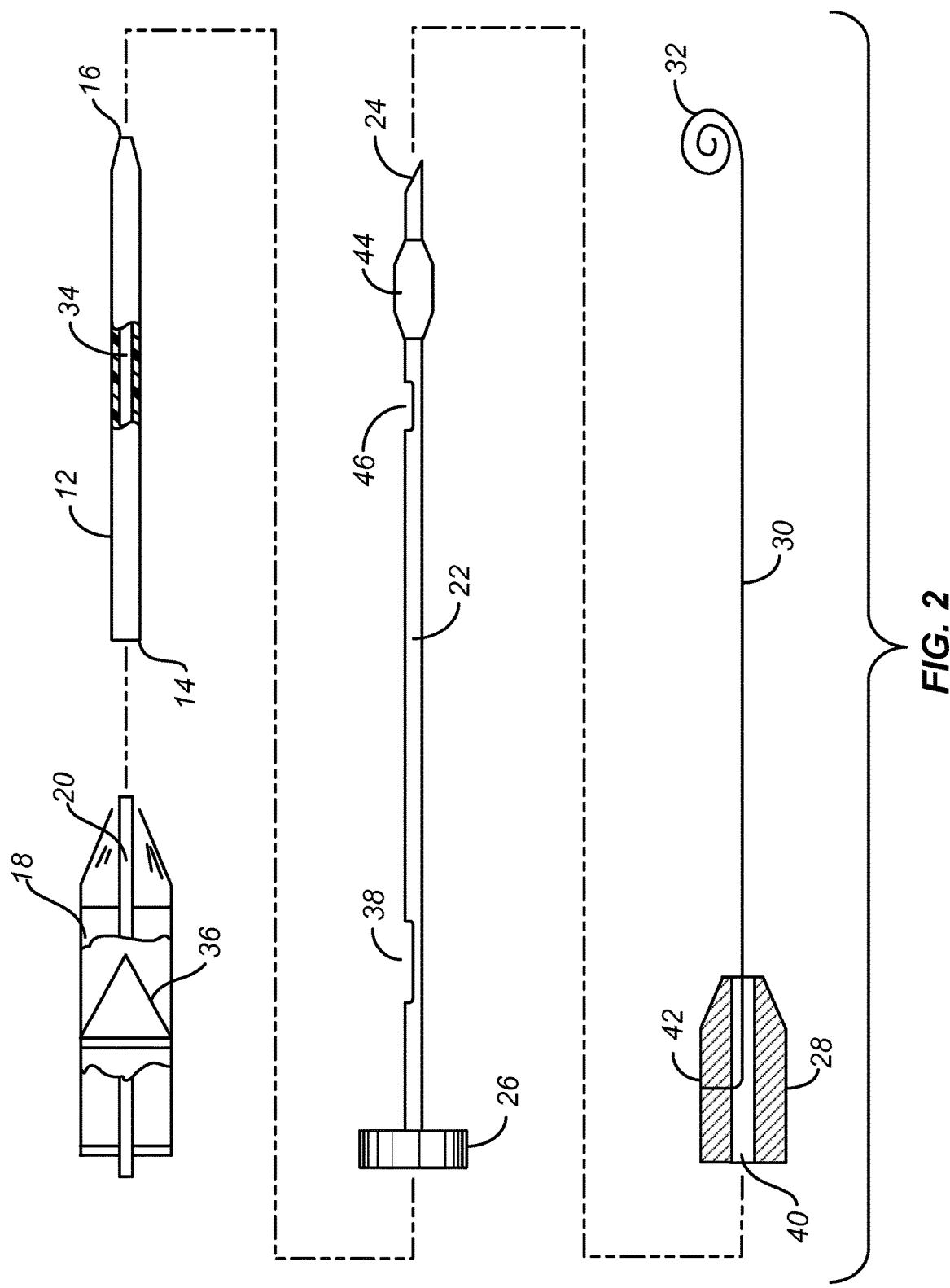
FIG. 2 is an exploded view of the intravenous catheter and needle assembly of FIG. 1.
Figure 3:
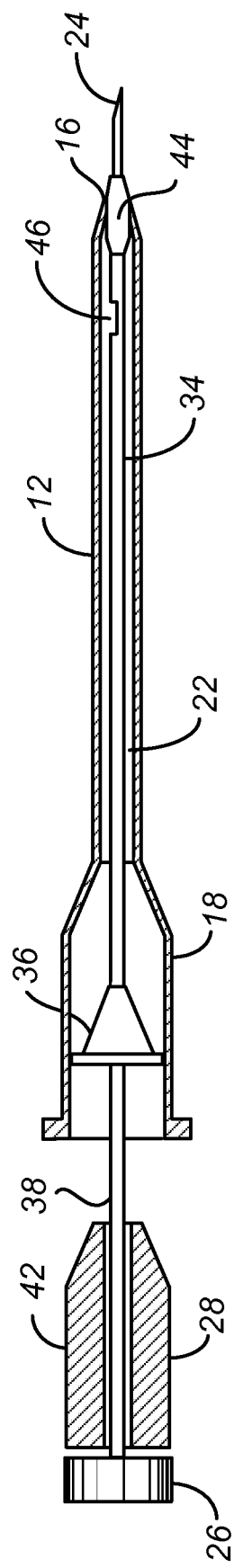
FIG. 3 is an axial cross-sectional view of the intravenous catheter and needle assembly of FIGS. 1 and 2.

As shown in FIGS. 1-3, an exemplary intravenous catheter and needle assembly 10 constructed in accordance with the principles of the present invention comprises a catheter body 12 having a proximal end 14 and a distal end 16. A proximal hub 18 is attached to the proximal end 14 of the catheter body and includes a pair of attachment wings 20 which are used to secure the catheter hub to a patient's skin in the conventional manner after the catheter has been introduced into a target vein or other blood vessel.

The catheter body 12 has a central lumen 34 (FIG. 2) which slidably receives an access needle 22 having a tissue-penetrating distal tip 24 which extends distally from the distal end 16 of the catheter body 12 when the assembly is ready for use. The tissue-penetrating tip will usually be a sharpened needle-type or trocar-type tip but could alternatively be a radiofrequency electrode or other energy-enhanced penetrating element. A proximal grip 26 is attached to a proximal end of the needle 22 so that a user can grip and hold the needle as a slider 28 is advanced over the needle, as will be described in more detail below. The slider 28 is attached to a proximal end of a guidewire 30 (FIG. 2), and the guidewire 30 usually has a safety tip 32 at its distal end, typically being a planar coil as illustrated. The proximal hub 18 will usually have a hemostasis valve 36 in its interior where the hemostasis valve can receive the needle 22, as best seen in FIG. 3.

The slider 28 will be slidably mounted over the exterior of the needle 22, as best seen in FIG. 3. The guidewire 30 will be present in a central passage (not shown) of the access needle, and the slider 28 is slidably mounted over a proximal portion of the needle. A link 42 attached to the slider 28 passes through a slot 38 in the proximal region of the needle so that translation of the slider 28 in a distal direction causes distal safety tip 32 of the guidewire 30 to advance axially out the distal tip 24 of the needle, as shown in broken line in FIG. 1, while retraction of the slider 28 in a proximal direction fully withdraws the guidewire into the needle so that the guidewire is not visible outside of the needle.

When the access needle 22 is introduced into the lumen 34 of the catheter 12, as shown in FIG. 3, a tapered dilator element 44 which is coaxially disposed over a distal portion of the needle sits in an open distal end of the lumen 34 of the catheter body 12. The tapered dilator element 44 provides a tapered transition from the small diameter needle, typically having an outer diameter from 0.3 mm to 1.7 mm, usually from 0.4 mm to 1.7 mm, to the larger diameter of the catheter body 12, typically from 0.4 mm to 2.8 mm, usually from 0.9 mm to 2.5 mm. Often, the distal end of the catheter body 12 will also be tapered to further assist in the transition, and the tapered dilator element 44 will act to fill or occupy an annular gap between the outer diameter of the needle and the inner diameter of the catheter lumen.

The tapered dilator element 44 also helps to properly position the needle distal tip so that a short distal segment, typically in the range from 0.1 mm to 5 mm, preferably from 0.2 mm to 0.4 mm, extends distally beyond the distal end 16 of the catheter, as shown in FIG. 3. A blood perfusion port 46 is formed in the needle just proximally of the seal 44 so that the blood entering the distal tip 24 of the needle (when the needle is introduced to a vein or other blood vessel) will flow out through the port 46 and provide blood "flashback" flow to a transparent or translucent region or window 50 near the distal end of the catheter body 12. The short distance between the needle tip and the port 46 assures that "flashback" occurs rapidly so that the user knows immediately when the needle has entered the vein.

Figure 4A:
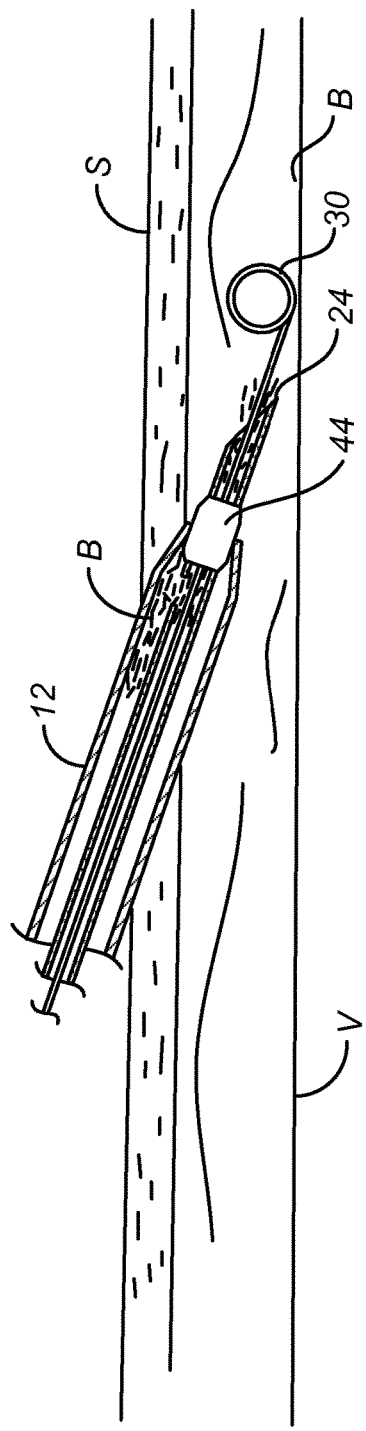
FIGS. 4A through 4B illustrate use of an intravenous catheter and needle assembly for introducing a catheter into a vein in accordance with the principles of the methods of the present invention.
Figure 4B:
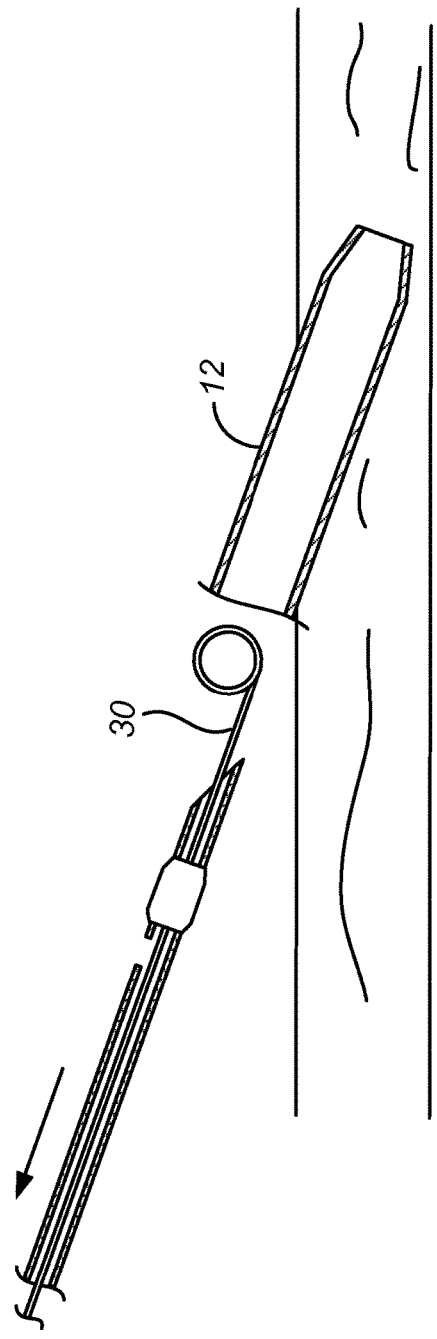

Referring now to FIGS. 4A-4B, the needle tip 24 and distal end of catheter body 12 are manually advanced by a user so that distal tip 24 of access needle 22 is penetrated through the patient's skin S, as shown in FIG. 4A. Once the needle tip 24 and the distal end of the catheter body 12 enter the vein V, as shown in FIG. 4A, blood will flow through lumen 52 of the needle in a proximal direction toward flashback port 46. Once the blood B reaches the flashback port 46, the blood will flow radially outward into the lumen 34 of the catheter body 12. The blood will then be visible to the user through the transparent/translucent region 50, alerting the user the needle tip has entered the vein.

Once the needle tip 24 and the distal end of the catheter body 12 are in the vein, the user may optionally advance the safety tip of guidewire 30, allowing the needle and catheter to be further advanced into the vein while minimizing the risk of accidentally puncturing the vein wall. Once the catheter 12 is in a desired position, the needle 22 and guidewire 30 may be withdrawn (FIG. 4B), leaving the catheter in place for use.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method, comprising:
   obtaining a medical device, comprising:
   a catheter; and
   a needle including a dilating element permanently attached to an exterior of the needle at a distal portion of the needle proximate a tissue-penetrating distal end thereof, the dilating element having an outer diameter equal to or greater than a diameter of an opening at a distal end of the catheter, the needle situated in a first medical device position such that at least a portion of the dilating element is in the opening and the tissue-penetrating distal end is distal of the opening;
   penetrating a vein with the tissue-penetrating distal end of the needle;
   moving the distal end of the catheter into the vein;
   advancing the catheter into the vein over the needle; and
   removing the needle from the catheter.

2. The method according to claim 1, wherein the needle includes a flashback port proximal of the dilating element, and wherein the catheter includes a transparent or translucent region proximate the distal end thereof, the method further comprising observing blood through the transparent or translucent region after the penetrating step, but before the moving step, to ensure that the distal end of the needle is within the vein.

3. The method according to claim 1, wherein the medical device further comprises a guidewire, the method further comprising inserting at least a distal end of the guidewire through the tissue-penetrating distal end of the needle and into the vein prior to the advancing step.

4. The method according to claim 3, wherein the guidewire includes a safety tip with a coiled configuration, wherein the inserting step comprises inserting the safety tip into the vein, the safety tip transitioning from a straight configuration in the needle to the coiled configuration in the vein.

\* \* \* \* \*